United States Patent
Pan et al.

(10) Patent No.: US 8,167,614 B2
(45) Date of Patent: May 1, 2012

(54) APPARATUS AND METHOD OF IRREGULAR BONE DEFECT DETECTION OF DENTAL IMPLANT

(75) Inventors: Min-Chun Pan, Taoyuan County (TW); Han-Bo Chuang, Kaohsiung County (TW); Shyh-Yuan Lee, Taipei (TW)

(73) Assignee: National Central University, Taoyuan County (TW)

( * ) Notice: Subject to any disclaimer, the term of this patent is extended or adjusted under 35 U.S.C. 154(b) by 0 days.

(21) Appl. No.: 13/048,450

(22) Filed: Mar. 15, 2011

(65) Prior Publication Data

US 2011/0165538 A1 Jul. 7, 2011

Related U.S. Application Data

(63) Continuation-in-part of application No. 12/329,569, filed on Dec. 6, 2008, now abandoned.

(30) Foreign Application Priority Data

Dec. 6, 2007 (TW) ................................ 96146553 A

(51) Int. Cl.
*A61C 19/04* (2006.01)
(52) U.S. Cl. .......................................... 433/72; 600/552
(58) Field of Classification Search .................... 433/72, 433/215; 600/589, 590, 552, 553; 33/513
See application file for complete search history.

(56) References Cited

U.S. PATENT DOCUMENTS

| 5,392,779 | A | * | 2/1995 | Meredith et al. | .............. | 600/437 |
| 5,690,486 | A | * | 11/1997 | Zigelbaum | ...................... | 433/29 |
| 7,147,467 | B2 | | 12/2006 | Shoji et al. | | |
| 2002/0143268 | A1 | * | 10/2002 | Meredith et al. | .............. | 600/552 |
| 2006/0281042 | A1 | * | 12/2006 | Rizoiu et al. | .................... | 433/29 |
| 2009/0018419 | A1 | * | 1/2009 | Torch | ............................. | 600/318 |

OTHER PUBLICATIONS

Zhuang, H. B. et al., Irregular bone defect detection and device on dental implants, Proceeding of the 2010 Design of Medical Devices Conference (DMD 2010, Apr. 13-15, 2010, Minneapolis, MN, USA) (DMD2010-3870), Journal of Medical Devices, Transactions of the ASME, vol. 4, No. 2, pp. 027521.
Zhuang, H. B. et al, Design and implementation of noncontact measurement device for irregular dental osseointegration detection, Proceeding of the 2011 Design of Medical Devices Conference (DMD 2011, Apr. 12-14, 2011, Minneapolis, MN, USA) (DMD2011-5280).

* cited by examiner

*Primary Examiner* — Cris L Rodriguez
*Assistant Examiner* — Eric Rosen
(74) *Attorney, Agent, or Firm* — Jackson IPG PLLC; Demian K. Jackson

(57) ABSTRACT

A non-contact apparatus and method detect irregular bone defects around a dental implant. Structural resonance frequency is produced and received to recognize a quality, a direction and a depth of an irregular bone defect. Thus, an interfacial osseointegration can be evaluated, and the present invention is of great help to assess osseointegration and diagnosis interfacial bone defects after the dental surgery.

14 Claims, 7 Drawing Sheets

APPARATUS AND METHOD OF IRREGULAR BONE DEFECT DETECTION OF DENTAL IMPLANT

CROSS-REFERENCE TO RELATED APPLICATION

This application claims priority to under 35 U.S.C. §120 and is a continuation-in-part of U.S. application Ser. No. 12/329,569, filed Dec. 6, 2008, now abandoned the entire contents of which are fully incorporated herein by reference.

FIELD OF THE INVENTION

The present invention relates to bone defect detection; more particularly, relates to quantitatively evaluating an osseointegration between a dental implant and an alveolar bone through differences of dynamic characteristics of a dental implant and irregular bone defects and furthermore obtaining quality, direction and depth of bone defect.

DESCRIPTION OF THE RELATED ARTS

General devices for detecting implant stability or bone defect use non-destructive method with vibration. Among these methods, impulse force or sinusoidal wave is used to vibrate a dental implant to evaluate integrity between a dental implant and an alveolar bone through analyzing a resonance frequency.

A prior art is a U.S. Pat. No. 5,392,779. The first prior art provides a method and apparatus for testing an implant attached to a human or animal bone, where the apparatus has a transducer for vibrating the implant; and a resonance frequency is detected to evaluate integrity of the attachment between the implant and the bone. Another prior art is a U.S. No. 2002/0143268A1 patent. The prior art comprises a device with a transducer; a connector connected with the device; and a memory device for storing detected data, where the device vibrates a bone implant through the transducer to obtain a stability of the bone implant through analyzing a resonance response of the vibration. And, another prior art is a U.S. Pat. No. 7,147,467. The prior art provides a measurement instrument for obtaining a tooth mobility, comprising a device for hitting a tooth; a sensor for sensing a movement of a tooth; and a device for calculating the mobility of the tooth on the basis of an output signal from the sensor.

The above prior arts provides methods for detecting implant stability through vibration non-destructively, yet only overall integrity between a dental implant and an alveolar bone is obtained, but not quality, direction and depth of bone defect. Additionally, although a clinical X-ray device can be used to obtain quality of bone defect, detecting through a X-ray device is an invasive detection and 2-dimentional image thus obtained has a limit on diagnosis of defective direction and depth. Conclusively, these prior arts do not solve all problems on diagnosing an interfacial osseointegration. Hence, the prior arts do not fulfill all users' requests on actual use.

SUMMARY OF THE INVENTION

The main purpose of the present invention is to quantitatively obtain an osseointegration status between a dental implant and an alveolar bone and to detect a quality, a direction and a depth of a bone defect.

Another purpose of the present invention is to evaluate a connected strength of an implant-bone interface through analyzing an osseointegration status between a dental implant and an alveolar bone.

To achieve the above purpose, the present invention is a non-contact apparatus and method of irregular bone defect detection around a dental implant. The apparatus comprises a metal attachment, a non-contact detecting probe, a transducer-detector driver unit and a detecting instrument. The apparatus has a method comprising steps of: (a) locking the metal attachment on a dental implant and connecting the non-contact detecting probe to the transducer-detector driver to enfold the metal attachment; (b) connecting the transducer-detector driver unit to the detecting instrument directly or through a cable line and connecting the detecting instrument to a personal computer through a USB cable while the personal computer is used to control operations of the detecting instrument and testee data are transferred to the personal computer to be managed; (c) producing a non-contact sound wave by a sound-wave vibration producing device of the detecting instrument with a non-contact sound transducer of the detecting probe through the transducer-detector driver unit to vibrate the metal attachment, sensing and receiving a vibration signal through a micro accelerometer or a non-contact displacement sensor of the non-contact detecting probe, and transmitting the vibration signal to a structural-response receiver and frequency analyzer unit of the detecting instrument through the transducer-detector driver unit to be analyzed; and (d) transforming the analyzed vibration signal to a digital signal to be transmitted to a processor of the detecting instrument, figuring out the values of both resonance frequencies and the locations of interfacial bone defects by the processor, displaying the calculated data on an LCD, and storing the calculated data in a memory. Accordingly, a novel non-contact apparatus and method of irregular bone defect detection around a dental implant is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
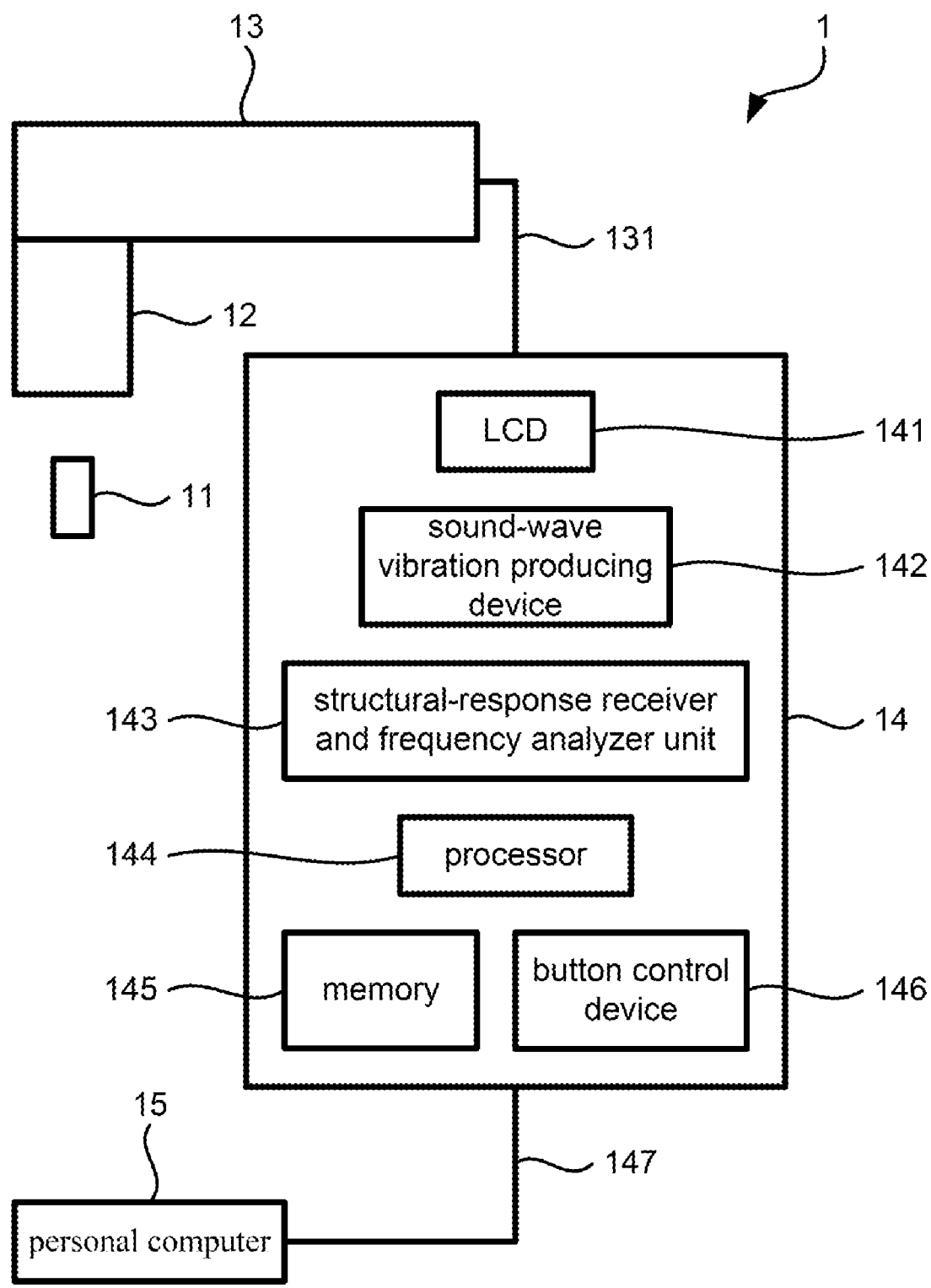
FIG. 1 is the structural view showing the preferred embodiment according to the present invention.

Please refer to FIG. 1, which is a structural view showing a preferred embodiment according to the present invention. As shown in the figure, the present invention is a non-contact apparatus and method of irregular bone defect detection around a dental implant, where the apparatus 1 comprises a metal attachment 11, a non-contact detecting probe 12, a transducer-detector driver unit 13 and a detecting instrument 14.

The metal attachment 11 is made of a biocompatibility metal material with a pillar shape, and it has a thread at bottom to be locked on a dental implant when the detection is performed. A thread of the metal attachment 11 is changeable according to a dental implant.

The non-contact detecting probe 12 comprises a non-contact sound transducer at a transmitting end and a micro accelerometer or a non-contact displacement sensor at a receiving end to enfold the metal attachment 11 for non-contact sound-wave excitation and vibration signal receiving; the non-contact detecting probe 12 has a changeable size according to the metal attachment 11; and the non-contact detecting probe 12 has a transducer-detector changeable according to detection precision.

The transducer-detector driver unit 13 is connected with the non-contact detecting probe 12 at an end; and is connected with the detecting instrument 14 at another end through a cable line 131, where the transducer-detector driver unit 13 can also be connected with the detecting instrument 14 directly without the cable line 131.

The detecting instrument 14 comprises a liquid crystal display (LCD) 141, a sound-wave vibration producing device 142, a structural-response receiver and frequency analyzer unit 143, a processor 144, a memory 145 and a button control device 146. And the detecting instrument 14 is connected with a personal computer 15 through a universal serial bus (USB) cable 147. Therein, the detecting instrument 14 is built-in with a lithium battery rechargeable through a 110-volt socket or a USB jack; and displays a value of a resonance frequency, a discriminating location of an interfacial bone defect, a capacity of the memory and a capacity of the battery. The sound-wave vibration producing device 142 produces a non-contact sound wave with a frequency between 1 kHz and 20 kHz. And, the personal computer 15 transmits detected data through the USB cable 147; and controls the detecting instrument 14 through a computer operation interface for detection. Thus, with the above structure, a novel non-contact apparatus of irregular bone defect detection around a dental implant is obtained.

Figure 2:
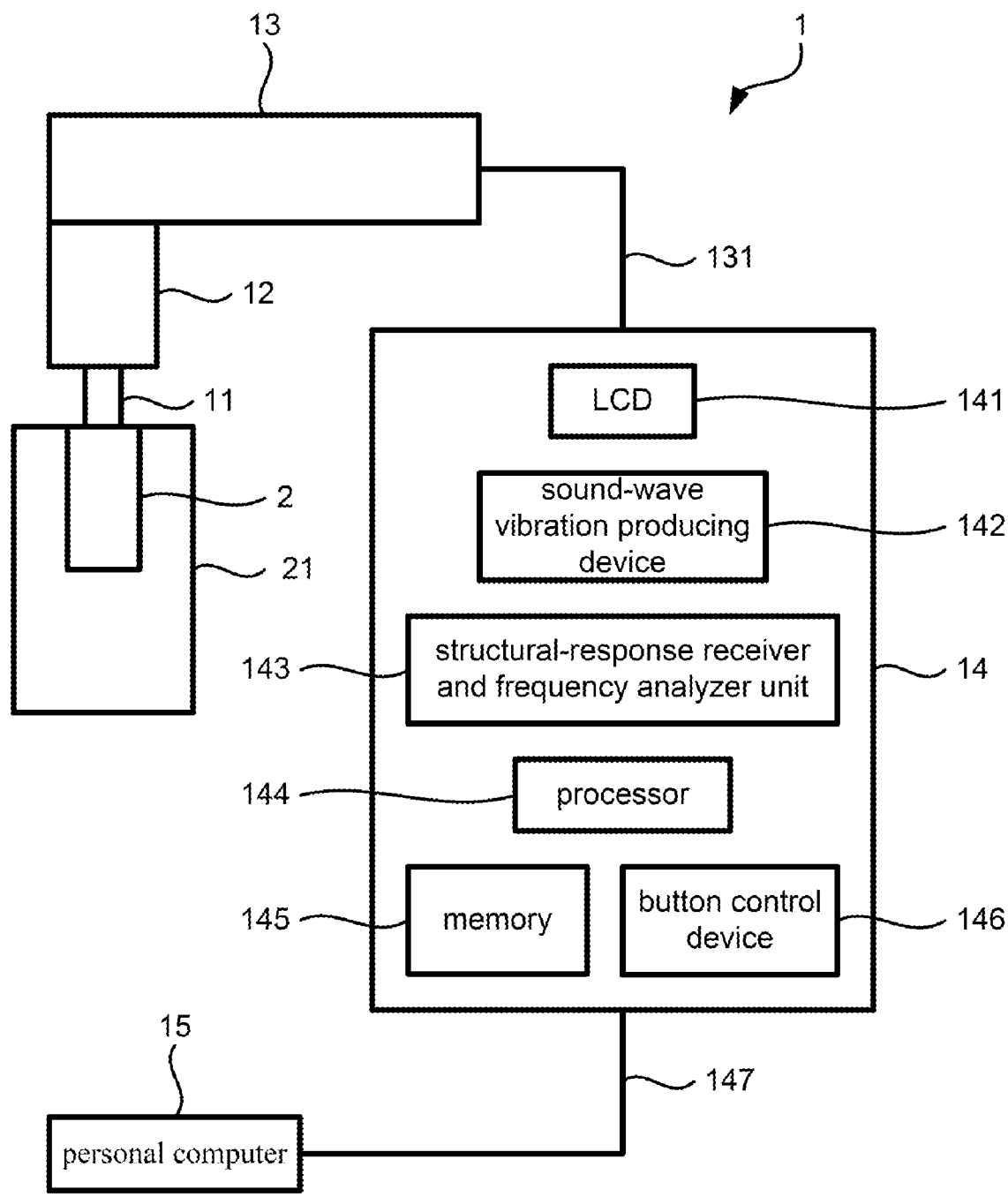
FIG. 2 is the view showing the status of use.
Figure 3:
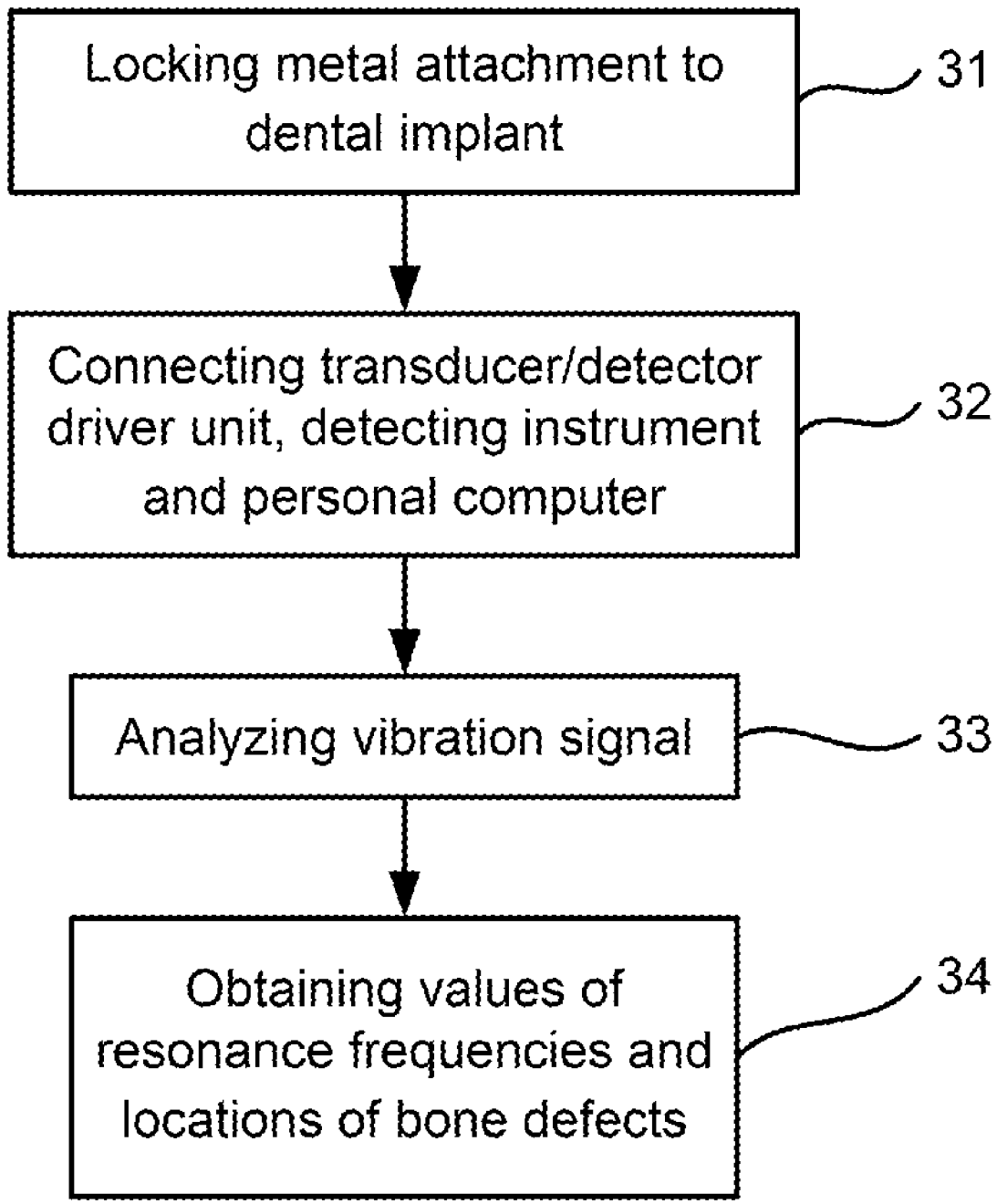
FIG. 3 is the view showing the detection flow.
Figure 4:
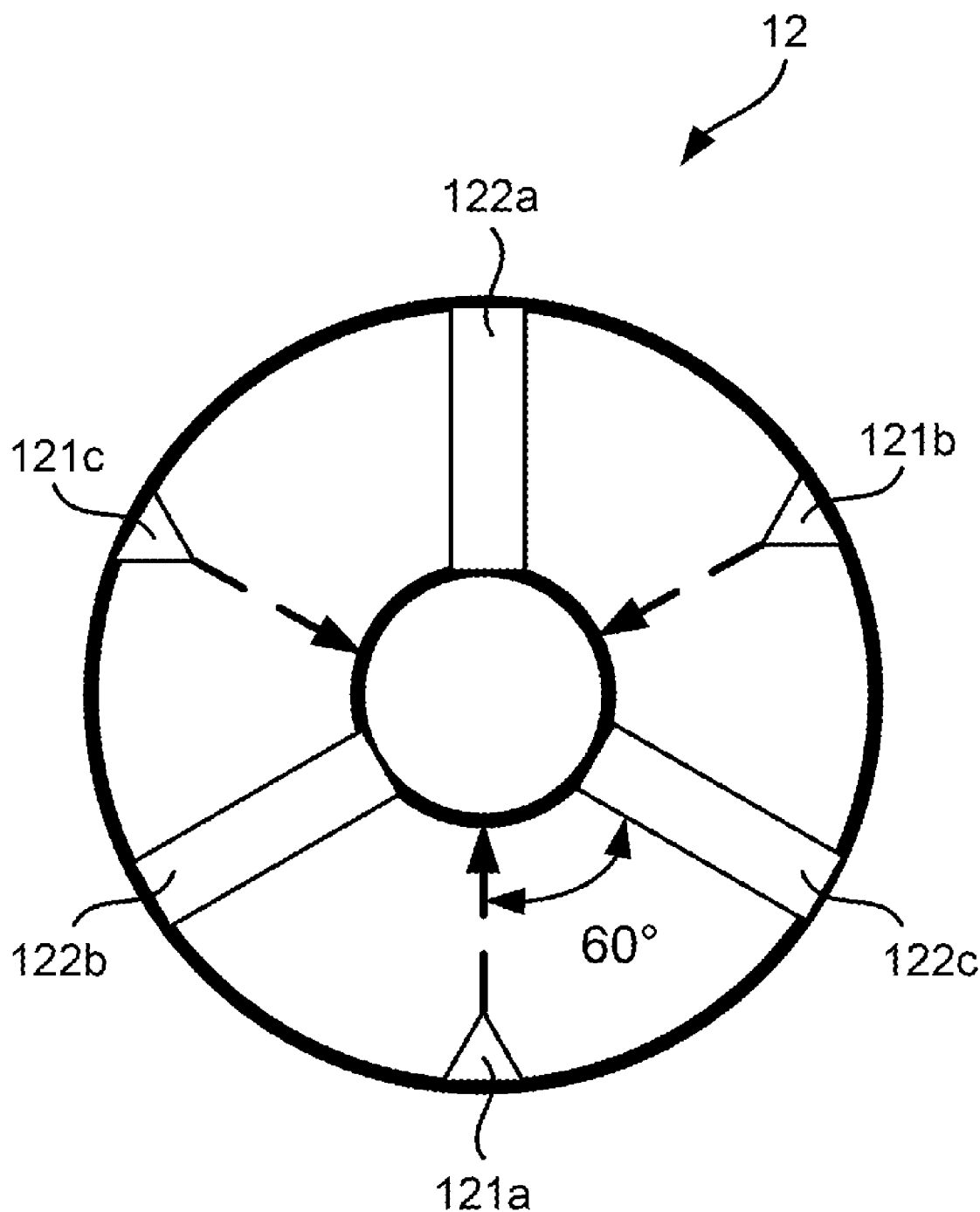
FIG. 4 to FIG. 7 are the views showing the preferred embodiment of the non-contact detecting probe.
Figure 5:
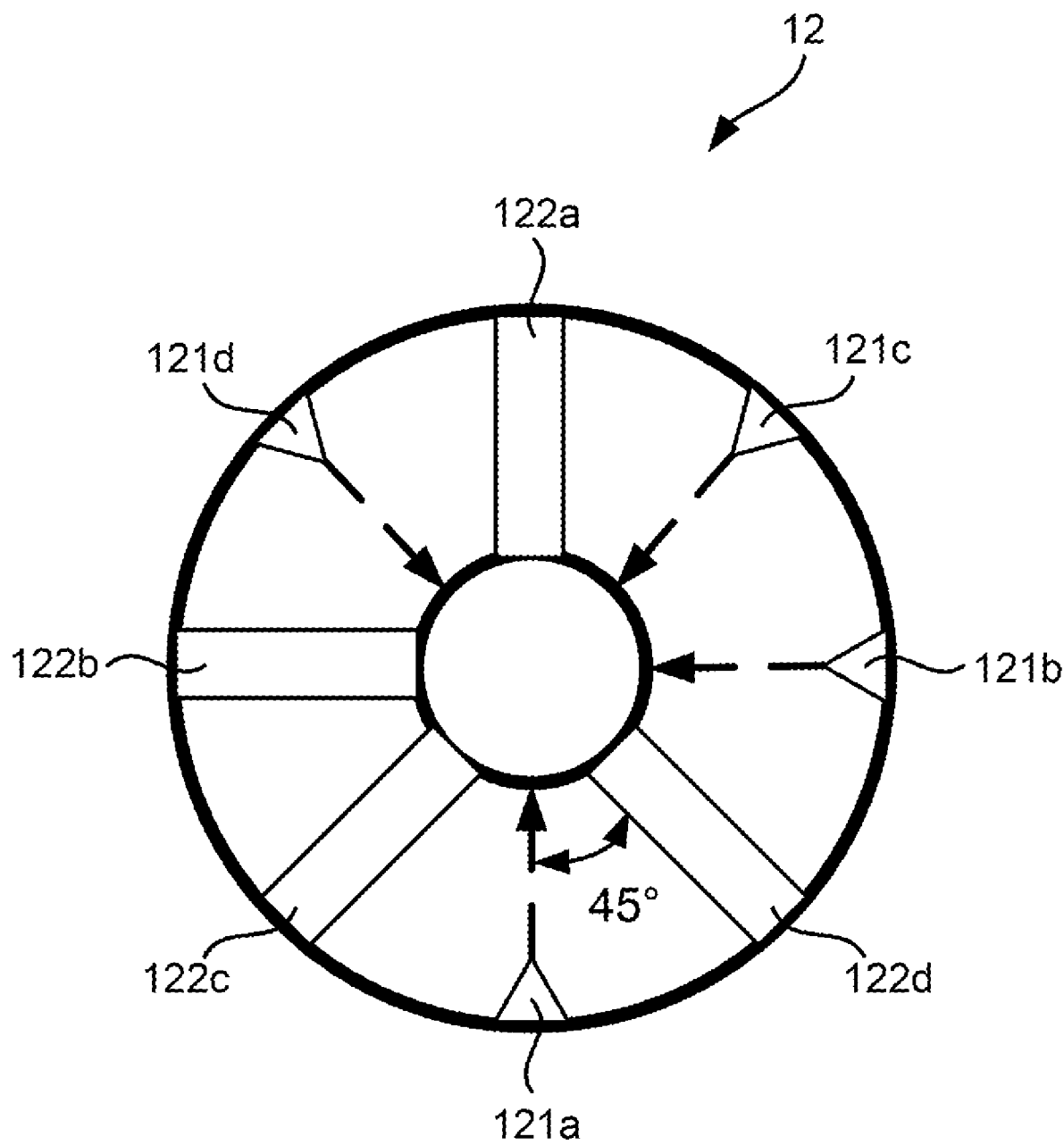
Figure 6:
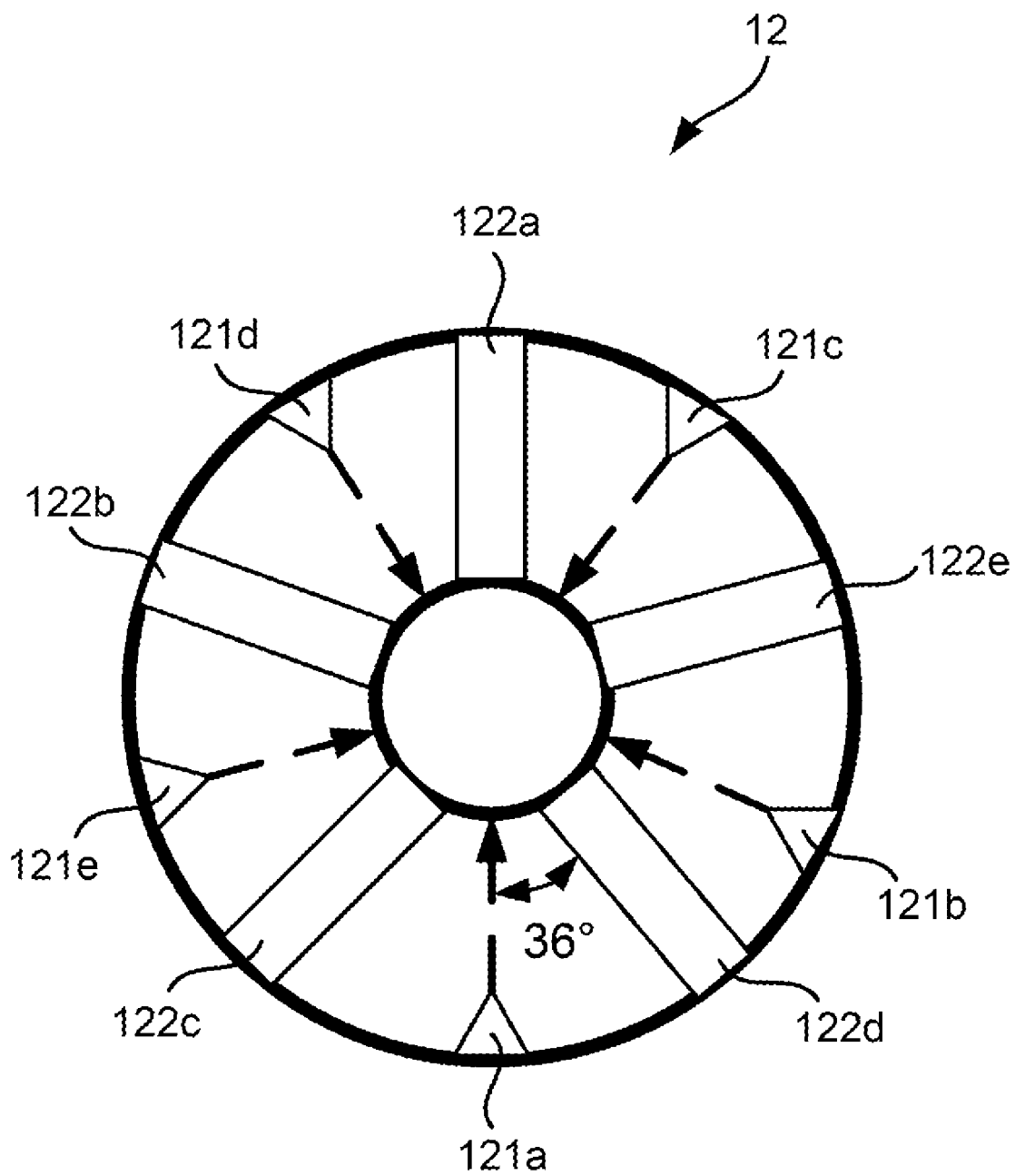
Figure 7:
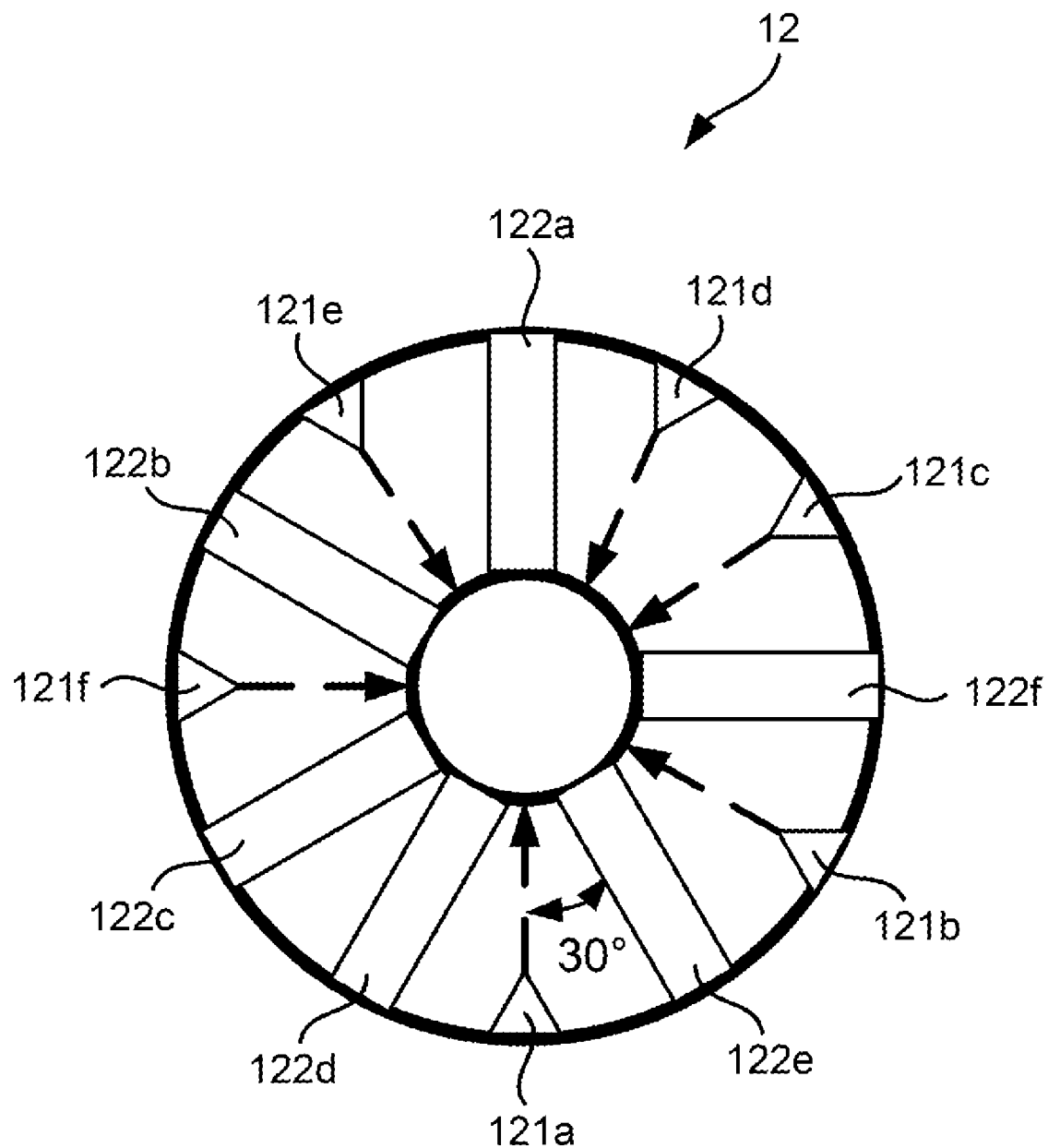

Please refer to FIG. 2 and FIG. 3, which are views showing a status of use and a detection flow. As shown in the figures, a non-contact method is used for detecting a dental implant 2 that is embedded with a bone 21 using a non-contact apparatus 1 according to the present invention, which comprises the following steps:

(a) Locking metal attachment to dental implant 31: A metal attachment 11 is first locked on the dental implant 2. Then, a non-contact detecting probe 12 and a transducer-detector driver unit 13 are connected together, and are used to enfold the metal attachment 11.

(b) Connecting transducer-detector driver unit, detecting instrument and personal computer 32: The transducer-detector driver unit 13 is connected with a detecting instrument 14 through a cable line 131; and, the detecting instrument 14 is connected with a personal computer 15 through a USB cable 147. And, the personal computer 15 is used to control operations of the detecting instrument 14; and testee data are transferred to the personal computer 15 to be managed. Therein, the transducer-detector driver unit 13 can be connected with the detecting instrument 14 directly, and the detecting instrument 14 can be operated alone.

(c) Analyzing vibration signal 33: A non-contact sound wave is produced by a sound-wave vibration producing device 142 of the detecting instrument 14 with a non-contact sound transducer of the non-contact detecting probe 12 through the transducer-detector driver unit 13 to vibrate the metal attachment 11. A vibration signal is thus sensed and received through a micro accelerometer or a non-contact displacement sensor of the non-contact detecting probe 12. Then the vibration signal is transmitted to a structural-response receiver and frequency analyzer unit 143 of the detecting instrument 14 through the transducer-detector driver unit 13 to be analyzed.

(d) Obtaining values of resonance frequencies and locations of bone defects 34: After the analysis, the vibration signal is transformed to a digital signal to be transmitted to a processor 144 of the detecting instrument 14. Then the values of resonance frequencies sensed by a micro accelerometer or a non-contact displacement sensor and the locations of interfacial bone defects are figured out by the processor 144. Then the calculated resonance frequency value and the discriminated interfacial bone defect location are displayed on an LCD 141 and are stored in a memory 145.

In step (d), a button control device 146 of the detecting instrument 14 transmits a control signal to the processor 144 for selection or adjustment through buttons, such as changing a frequency range of a non-contact sound wave, adding storage data, deleting storage data, or controlling a pair of a non-contact sound transducer and a micro accelerometer or a non-contact displacement sensor. Hence, a synchronous or direction-changing detection is processed as needed.

Please refer to FIG. 4 to FIG. 7, which are views showing preferred embodiments of a non-contact detecting probe 12. As shown in the figures, on using the present invention, a first to a fourth preferred embodiments of a non-contact detecting probe 12 are designed to be used according to requirements. The non-contact detecting probes 12 includes a set of three pairs of the non-contact sound transducer and the micro accelerometer (or the non-contact displacement sensor) 121*a*,121*b*,121*c*/122*a*, 122*b*,122*c* with a separation of a 60-degree angle; a set of four pairs of the non-contact sound transducer and the micro accelerometer (or the non-contact displacement sensor) 121*a*,121*b*,121*c*, 121*d*/122*a*,122*b*, 122*c*,122*d* with a separation of a 45-degree angle; a set of five pairs of the non-contact sound transducer and the micro accelerometer (or the non-contact displacement sensor) 121*a*,121*b*,121*c*,121*d*, 121*e*/122*a*,122*b*,122*c*,122*d*,122*e* with a separation of a 36-degree angle; and a set of six pairs of the non-contact sound transducer and the micro accelerometer (or the non-contact displacement sensor) 121*a*,121*b*, 121*c*,121*d*,121*e*,121*f*/122*a*,122*b*,122*c*, 122*d*,122*e*,122*f* with a separation of a 30-degree angle. The non-contact detecting probes 12 use a non-destruct and non-invasive detection method, where a non-contact sound excitation is used and non-contact detecting probes are used to emit and receive vibration signals. Thus, values of resonance frequencies are detected to be summarized for obtaining a relationship between structural resonance frequencies and bone defects. Since frequency decreases as defect increases, quality, direction and depth of irregular bone defect are figured out with differences of structural resonance frequencies detected by the pairs of the non-contact sound transducer and the micro accelerometer (or the non-contact displacement sensor) at different angles. In addition, a firmness a connected strength and a stability of an interfacial osseointegration is thus evaluated. Hence, the present invention is of great help to assess osseointegration and diagnosis an interfacial bone defect after the dental surgery.

To sum up, the present invention is a non-contact apparatus and method of irregular bone defect detection around a dental implant, where an osseointegration status between a dental implant and an alveolar bone is evaluated quantitatively and a quality, a direction and a depth of a bone defect are detected for ensuring a connected strength of an implant-bone interface.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A detection apparatus for irregular bone defect detection around a dental implant, comprising:
   a metal attachment, said metal attachment configured to lock on a dental implant;
   a non-contact detecting probe, said non-contact detecting probe configured to enfold said metal attachment and to create and receive structural vibration, wherein vibration travels through an empty space between the non-contact detecting probe and the metal attachment;
   a transducer-detector driver unit, said transducer-detector driver unit connected to said non-contact detecting probe; and
   a detecting instrument, said detecting instrument directly connected to said transducer-detector driver unit or connected to said transducer-detector driver unit through a cable line at an end of said detecting instrument, said detecting instrument configured to connect to a personal computer through a universal-serial-bus (USB) cable at another end of said detecting instrument.

2. The apparatus according to claim 1, wherein said metal attachment is made of a biocompatibility metal material.

3. The apparatus according to claim 1, wherein said metal attachment has a thread at a bottom of the metal attachment; wherein said metal attachment has a pillar shape; and wherein the thread is interchangeable with other threads based on said dental implant.

4. The apparatus according to claim 1, wherein said non-contact detecting probe comprises a non-contact sound transducer at a transmitting end; and a micro accelerometer or a non-contact displacement sensor at a receiving end.

5. The apparatus of claim 1, wherein said non-contact detecting probe is interchangeable with a non-contact detecting probe of a different size based on said metal attachment; and wherein said non-contact detecting probe has a transducer-detector detector interchangeable with other transducer-detectors based on a detecting precision.

6. The apparatus according to claim 1, wherein said detecting instrument comprises a liquid crystal display (LCD), a sound-wave vibration producing device, a structural-response receiver and frequency analyzer unit, a processor, a memory and a button control device.

7. The apparatus according to claim 6, wherein said LCD is configured to display a value of a resonance frequency, a location of an interfacial bone defect, a capacity of said memory and a capacity of a battery.

8. The apparatus according to claim 6, wherein said sound-wave vibration producing device is configured to produce a non-contact sound wave having a frequency between 1 kHz and 20kHz.

9. The apparatus according to claim 6, wherein said structural-response receiver and frequency analyzer unit is configured to receive a vibration signal detected by a micro accelerometer or a non-contact displacement sensor; and wherein said structural-response receiver and frequency analyzer unit is configured to analyze and transform said vibration signal into a digital signal.

10. The apparatus according to claim 6, wherein said button control device is configured to output a control signal to said processor; and wherein said button control device comprises buttons configured to operate an action selected from a group consisting of changing a frequency range of a non-contact sound wave, adding storage data, deleting storage data, controlling a non-contact sound transducer, and controlling a micro accelerometer or a non-contact displacement sensor.

11. The apparatus according to claim 10, wherein said processor is configured to receive said control signal to obtain functions selected from a group consisting of selection and adjustment.

12. The apparatus according to claim 1, wherein said detecting instrument is directly connected with said transducer-detector driver unit.

13. The apparatus according to claim 1, wherein said detecting instrument is built-in with a rechargeable lithium battery.

14. The apparatus according to claim 1, wherein said apparatus is configured to implement a method comprising steps of:

(a) locking said metal attachment on said dental implant first and then connecting said non-contact detecting probe to said transducer-detector driver unit and enfolding said non-contact detecting probe around said metal attachment;

(b) connecting said transducer-detector driver unit to said detecting instrument directly or through a cable line and connecting said detecting instrument to a personal computer through said USB cable;

(c) producing a non-contact sound wave by a sound-wave vibration producing device of said detecting instrument with a non-contact sound transducer of said non-contact detecting probe through said transducer-detector driver unit to vibrate said metal attachment; receiving a vibration signal through a micro accelerometer or a non-contact displacement sensor; and transmitting said vibration signal to a structural-response receiver and frequency analyzer unit through said transducer-detector driver unit to be analyzed; and (d) transmitting analyzed data to a processor to calculate values of resonance frequencies and locations of interfacial bone defects to display on a LCD and store the calculated resonance frequencies and bone defect locations in a memory.

* * * * *